| United States Patent [19] | [11] | 4,203,996 |
|---|---|---|
| Mikolajczak et al. | [45] | May 20, 1980 |

[54] SYNTHETIC CEPHALOTAXINE ESTERS HAVING ANTILEUKEMIC P388 ACTIVITY

[75] Inventors: Kenneth L. Mikolajczak, Washington; Cecil R. Smith, Jr., Dunlap, both of Ill.

[73] Assignee: The United States of America as represented by the Secretary of Agriculture, Washington, D.C.

[21] Appl. No.: 738

[22] Filed: Jan. 3, 1979

Related U.S. Application Data

[62] Division of Ser. No. 880,000, Feb. 22, 1978, Pat. No. 4,152,333.

[51] Int. Cl.$^2$ .............................................. A61K 31/40
[52] U.S. Cl. .................................................... 424/274
[58] Field of Search ........................................ 424/274

*Primary Examiner*—Jerome D. Goldberg
*Attorney, Agent, or Firm*—M. Howard Silverstein; David G. McConnell; Curtis P. Ribando

[57] ABSTRACT

Six acyl esters of cephalotaxine have been synthesized by ordinary and standard procedures, and all have demonstrated chemotherapeutic activity against leukemia of the strain P388 in animals.

7 Claims, No Drawings

SYNTHETIC CEPHALOTAXINE ESTERS HAVING ANTILEUKEMIC P388 ACTIVITY

CROSS-REFERENCE TO RELATED APPLICATION

This is a divisional application of Ser. No. 880,000, filed on Feb. 22, 1978, now U.S. Pat. No. 4,152,333.

BACKGROUND OF THE INVENTION

1. Field of the Invention

This invention relates to a group of synthetic esters of cephalotaxine and the use of these esters as chemotherapeutic agents for the remission of leukemia of the strain P388 in animals.

2. Description of the Prior Art

Among the alkaloids which have been isolated from *Cephalotaxus harringtonia* plant material are cephalotaxine and a number of its esters [Powell et al., Tetrahedron Lett. 4081 (1969); Powelll et al., Tetrahedron Lett. 815 (1970); Mikolajczak et al., Tetrahedron 28: 1995 (1972); U.S. Pat. No. 3,793,454; and U.S. Pat. No. 3,870,727]. Though cephalotaxine itself is inactive, some of its esters which are derived from relatively complex dicarboxylic acid moieties have been found to exhibit significant activity aginst experimental leukemia systems [Powell et al., J. Pharm. Sci. 61(8): 1227–1230 (August 1972)]. Two of the esters, harringtonine and homoharringtonine, have been approved for preclinical evaluation at the National Cancer Institute. However, plant material from which to extract the active esters is in critically short supply.

Cephalotaxine has been synthesized [Weinreb et al., J. Am. Chem. Soc. 97: 2503 (1975); Semmelhack et al., J. Am. Chem. Soc. 97: 2507 (1975); and Weinreb and Semmelhack, Acc. Chem. Res. 8: 158 (1975)] thereby stimulating efforts to convert it to some of its active, naturally occurring esters by reaction with appropriate acid compounds. However, very unfavorable steric (and perhaps electronic) intereactions at the reaction sites of both the cephalotaxine and the acyl moiety preclude direct esterification [Mikolajczak et al., J. Pharm. Sci. 63: 1280 (1974)]. By means of complicated and indirect routes, cephalotaxine has been converted to the active esters, deoxyharringtonine [U.S. Pat. No. 3,959,312; Mikolajczak et al., Tetrahedron Lett. 283 (1974); and Li et al., Hua Hsueh Hsueh Pao 33: 75 (1975)]; and harringtonine [Anonymous, K'o Hsueh T'ung Pao 20: 437 (1975); Chem. Abstr. 84: 105859Z (1976)].

SUMMARY OF THE INVENTION

We have now surprisingly found a group of synthetic acyl esters of cephalotaxine which show activity against leukemia of the strain P388 in animals, and which can be prepared from cephalotaxine by ordinary and standard procedures because they are not subject to the severe steric requirements of the prior art compounds. These alkaloid compounds are characterized by the following structural formula:

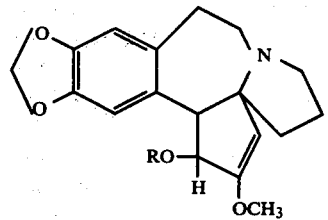

where R is selected from the group consisting of $$-\overset{O}{\overset{\|}{C}}-\overset{O}{\overset{\|}{C}}-OCH_2CH_3,$$

$$-\overset{O}{\overset{\|}{C}}-CH=CH-\overset{O}{\overset{\|}{C}}-OCH_3,$$

$$-\overset{O}{\overset{\|}{C}}-\overset{CH_2}{\overset{\|}{C}}-CH_2-\overset{O}{\overset{\|}{C}}-OCH_3,$$

$$-\overset{O}{\overset{\|}{C}}-CH=CH-CH=CH-CH_3,$$

$$O-\overset{O}{\overset{\|}{C}}-OCH_2OCl_3$$

$$-\overset{O}{\overset{\|}{C}}-CH-\underset{}{\bigcirc}, \text{ and}$$

$$-\overset{O}{\overset{\|}{C}}-OCH_2OCl_3.$$

It is therefore an object of this invention to obtain from cephalotaxine synthetic esters which have activity against leukemia.

Another object of the invention is to prepare these active cephalotaxine esters by ordinary and simple procedures.

It is also an object of the invention to administer the novel alkaloid compounds to animals in order to cause remission of leukemia of the strain P388 therein.

Other objects and advantages of the invention will become readily apparent from the ensuing description.

DETAILED DESCRIPTION OF THE INVENTION

Cephalotaxine is characterized by the following structural formula:

where R equals H. We have found that by substituting selected acyl groupings for the hydroxyl hydrogen, the chemotherapeutically inactive cephalotaxine can be converted to antileukemic alkaloids. It would appear from preliminary investigations that the activity of cephalotaxine esters is attributable primarily to the (−)-cephalotaxine enantiomer. This is the enantiomer ioslated from natural sources. Cephalotaxine produced synthetically, such as by one of the procedures taught in the references discussed above, occurs as a racemic mixture. While it is preferred to use the (−)-isomer, either isolated from plants or separated from a synthetic (±)-mixture, it is understood that the (±)-mixture itself would be a suitable starting material.

The acylating agents are preferably acid chlorides or anhydrides which are commercially available, or else readily obtainable by conventional modification of available precursor compounds, such as the appropriate acid, ester, or half ester. Such modifications are illustrated in the examples below.

Acylation and recovery procedures for obtaining the instant cephalotaxyl esters do not in themselves constitute novelty within the instant invention. However, these have been illustrated in detail in the accompanying examples for each of the disclosed species. It is understood that certain obvious alterations and variations of these procedures, involving the reagents, proportions, solvent systems, and other reaction conditions and parameters may be made without altering the nature of the final products. For instance, we have found that methyl cephalotaxyl fumarate

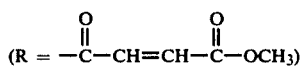

may be prepared with either methyl hydrogen fumarate or maleic anhydride as the acylating agent, due to isomerization of the double bond in the anhydride.

In the examples which follow, anhydrous reagents, solvents, and solutions of reactants were prepared by drying for at least 4 hours over type 3A or 4A molecular sieve. Extracts of aqueous systems were routinely dried with MgSO$_4$. All purification steps were monitored by thin layer chromatography, and in most instances by infrared analysis (IR). All the isolated cephalotaxine esters were amorphous solids, and each gave an IR, nuclear magnetic resonance, and mass spectrum (MS) consistent with its structure (see Table I for MS analysis). High-resolution mass spectral analyses were performed with a Nuclide 12-90G spectrometer.

EXAMPLE 1

Preparation of ethyl cephalotaxyl oxalate

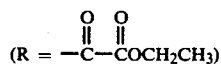

(−)-Cephalotaxine (5.0 g.) and 1.34 g. of pyridine in 20 ml. of anhydrous CH$_2$Cl$_2$ were cooled in an ice bath. Ethyl oxalyl chloride (2.38 g.) in 10 ml. of CH$_2$Cl$_2$ was added dropwise over 1 hour. Stirring at 0° C. was continued 3 more hours and then at room temperature overnight. The mixture was poured into 100 ml. of pH 7.0 phosphate buffer solution, and the solution was extracted with CH$_2$Cl$_2$. Evaporation of the CH$_2$Cl$_2$ afforded pure ethyl cephalotaxyl oxalate. The yield was 71% based on the (−)-cephalotaxine used.

EXAMPLE 2

Preparation of methyl cephalotaxyl fumarate

Fumaric acid (40.0 g.) in 50 ml. of anhydrous benzene and 75 ml. of dioxane was treated with 18 ml. (25% excess over the amount needed to esterify one carboxyl group) of MeOH and 2 ml. of concentrated H$_2$SO$_4$. The mixture was refluxed under a Dean-Stark trap until no more water collected in the trap, about 4 hours. The solvent was concentrated to 25 ml., water was added, and the mixture was extracted with diethyl ether. After evaporation of ether, the residue was separated in 3.0-g. batches on a 2.5×35 cm. column of silica gel with 300 ml. of ethyl acetate:benzene (10:90) followed by 400 ml. of ethyl acetate:benzene (20:80). Yield of methyl hydrogen fumarate was 15%.

Methyl hydrogen fumarate (3.22 g.) was treated overnight with stirring at room temperature with 10 ml. of oxalyl chloride. Excess oxalyl chloride was evaporated in vacuo, and the residue (the acid chloride) was dissolved in 10 ml. of CH$_2$Cl$_2$. A solution of 3.1 g. of (−)-cephalotaxine and 3 ml. of pyridine in 10 ml. of CH$_2$Cl$_2$ was added to the acid chloride slowly over 30 minutes., and the resulting solution stirred overnight. The mixture was poured into 75 ml. of 5% Na$_2$CO$_3$ solution and extracted with CH$_2$Cl$_2$. After evaporation of CH$_2$Cl$_2$, the residue was dissolved in diethyl ether:petroleum ether (75:25) and run through a 1×10 cm. neutral alumina (Woelm, grade III) column. The yield of methyl cephalotaxyl fumarate was 68% based on the (−)-cephalotaxine used.

EXAMPLE 3

Preparation of methyl cephalotaxyl itaconate

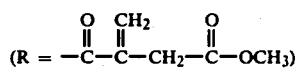

Itaconic acid (248 g.) was treated with 246 ml. of anhydrous methanol and 4.0 ml. acetyl chloride at reflux for 20 minutes. Excess MeOH was evaporated in vacuo and the residue was crystallized by adding 200 ml. of benzene, followed by 300 ml. of petroleum ether (b.p. 30°–60° C.) and chilling the solution to 0° C. The crystals were recrystallized from benzene:petroleum ether (3:2) and gave a m.p. of 66°–69° C. The yield of methyl hydrogen itaconate was 42% (115 g.).

Methyl hydrogen itaconate (3.17 g.) was dissolved in anhydrous ether and dried over type 4A molecular sieve. The ether solution was removed from the sieve and all solvent removed in vacuo. The residue was treated neat with 10 ml. of oxalyl chloride overnight at room temperature with stirring (magnetic). Excess oxalyl chloride was removed in vacuo and the acid chloride was dissolved in anhydrous CH$_2$Cl$_2$ and cooled in an ice bath. To this cold solution of the acid chloride was added dropwise a solution of 3.15 g. of (−)-cephalotaxine and 4 ml. of pyridine in 10 ml. of CH$_2$Cl$_2$. The mixture was allowed to warm to room temperature and was stirred overnight.

This mixture was poured into 50 ml. of 5% Na$_2$CO$_3$ solution, and the solution was extracted with CH$_2$Cl$_2$.

The crude product was dissolved in diethyl ether:CH₂Cl₂ (2:1) and was run through a neutral alumina (Woelm, grade III) column of 1×10 cm. The yield of pure methyl cephalotaxyl itaconate was 83% based on the (−)-cephalotaxine used.

EXAMPLE 4

Preparation of cephalotaxyl trans,trans-sorbate

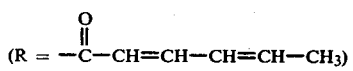

trans,trans-Sorbic acid (2.24 g.) was treated with oxalyl chloride for 2 hours. Excess oxalyl chloride was evaporated in vacuo. The residue was dissolved in 10 ml. of CH₂Cl₂ and cooled in an ice bath. A solution of 3.1 g. of (−)-cephalotaxine and 3 ml. of pyridine in CH₂Cl₂ (10 ml.) was added slowly (30 minutes) to the cold acid chloride solution and the mixture stirred at room temperature overnight. The mixture was poured into 75 ml. of 5% Na₂CO₃ solution and extracted with CH₂Cl₂. The crude product remaining after removal of CH₂Cl₂ was purified by chromatography on a 1×10 cm. neutral alumina (Woelm, grade III) column with diethyl ether. This was followed by chromatography on a silica gel column, 2.5×35 cm., with CH₂Cl₂. The yield of cephalotaxyl trans,trans-sorbate was 36% based on (−)-cephalotaxine used.

EXAMPLE 5

Preparation of cephalotaxyl L-mandelate, trichloroethylcarbonate

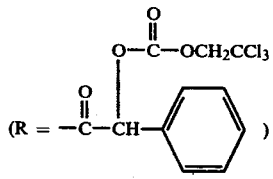

L-Mandelic acid (10 g.), 6.91 g. of benzyl alcohol, and 75 mg. of p-toluenesulfonic acid in 70 ml. of benzene was refluxed under a Dean-Stark trap for a total of 28 hours on 4 consecutive days. The crude benzyl ester was obtained by successively concentrating the liquor and cooling it to about 10° C. a number of times. The fractions melting between 97° C. and 105° C. were combined, dissolved in CHCl₃ and washed twice with 15 ml. portions of 5% aqueous NaHCO₃ solution. After evaporation of the CHCl₃, the product was recrystallized from benzene to give benzyl L-mandelate, m.p. 104°–106° C., yield 42%.

6.5 Grams of benzyl L-mandelate was dissolved in CH₂Cl₂ (25 ml.) and was treated dropwise with 5.90 g. of trichloroethoxycarbonyl chloride in 15 ml. of CH₂Cl₂. The mixture was stirred overnight at room temperature and then was poured into 75 ml. of 5% Na₂CO₃ solution and extracted with CH₂Cl₂. The crude product

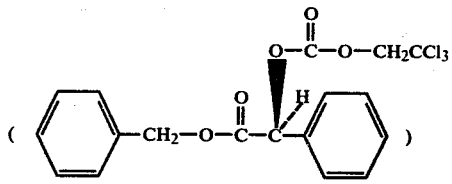

was purified by chromatography of 2 g. batches on a 2.5×35 cm. silica gel column with 200 ml. of benzene:petroleum ether, 25:75, 200 ml. of 35:65 and enough of 45:55 to completely elute the desired ester. The ester was then crystallized from diethyl ether at 0° C. to give a 68% yield of the trichloroethylcarbonate ester of benzyl L-mandelate, m.p. 96°–97° C. Hydrogenolysis of this ester (to remove the benzyl ester grouping) was done by hydrogenating 2 g. batches dissolved in 10 ml. of tetrahydrofuran with 200 mg. of 10% Pd/C until one molar equivalent of H₂ was consumed. This gave a 97% yield of

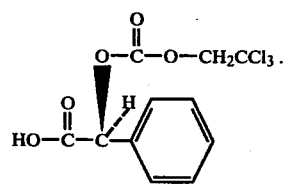

4.1 Grams of above acid was treated at reflux for 1 hour with 15 ml. of oxalyl chloride and the excess reagent removed in vacuo. The residue was dissolved in CH₂Cl₂ (20 ml.) and cooled in an ice bath. A solution of 2.52 g. of (−)-cephalotaxine and 2 ml. of pyridine in 20 ml. of CH₂Cl₂ was added slowly. The mixture was allowed to warm to room temperature and was then stirred overnight at room temperature. The mixture was poured into 75 ml. of 5% Na₂CO₃ solution which was then extracted with CH₂Cl₂. After evaporation of the CH₂Cl₂, the crude cephalotaxyl L-mandelate, trichloroethylcarbonate ester was run through a 1×10 cm. neutral alumina (Woelm, grade III) column in 2 -g. batches with diethyl ether. The yield was 91% based on (−)-cephalotaxine used.

EXAMPLE 6

Preparation of cephalotaxyl trichloroethylcarbonate

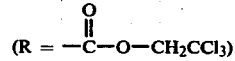

(−)-Cephalotaxine (2.40 g.) and 2 ml. of pyridine in 20 ml. of CH₂Cl₂ (anhydrous) was cooled in an ice bath. Then 1.80 g. of trichloroethoxycarbonyl chloride in 5 ml. of CH₂Cl₂ was added dropwise with stirring at 0° C. Stirring was continued at 0° C. for 3 more hours and then at room temperature overnight. The mixture was poured into 100 ml. of pH 7.0 phosphate buffer solution and the solution was extracted with CH₂Cl₂. Evaporation of the CH₂Cl₂ yielded pure cephalotaxyl trichloroethylcarbonate. The yield was 96% based on cephalotaxine used.

Table I

| Example | Isolated yield, %[a] | Formula | High resol. MS M+ calc. | M+ obsd. |
|---|---|---|---|---|
| 1 | 71 | $C_{22}H_{25}NO_7$ | 415.163 | 415.162 |
| 2 | 68 | $C_{23}H_{25}NO_7$ | 427.163 | 427.162 |
| 3 | 83 | $C_{24}H_{27}NO_7$ | 441.179 | 441.179 |
| 4 | 36 | $C_{24}H_{27}NO_5$ | 409.189 | 409.188 |
| 5 | 91 | $C_{29}H_{28}NO_8Cl_3$ | b | b |
| 6 | 96 | $C_{21}H_{22}NO_6Cl_3$ | 491.048 | 491.047 |

[a]Based on cephalotaxine; not optimized.
[b]$M^+ -191$ ($-C_3H_2O_3Cl_3$ group); calc. 432.179, obsd. 432.181.

Chemotherapeutic activity of each of the compounds prepared in Examples 1-6 was determined in mice which were implanted with lymphocytic leukemia cells of the strain P388, according to the National Cancer Institute Protocols [Geran et al., Cancer Chemother. Rep., Part 3, 3: 9 (1972)]. Starting 24 hours after the tumor implantation, previously determined dosages of each compound were injected intraperitoneally once a day for 9 days. The results are shown in Table II. Survival time of treated leukemic mice is compared to that of untreated leukemic mice (T/C×100). A T/C value of 100% indicates no activity. A T/C value greater than 100% means that the treated mice are surviving longer than the control mice. A compound giving a T/C value greater than or equal to 125% is indicative of activity as defined by the NCI Protocols, supra.

Table II

Biological Test Data for Activity of Cephalotaxine Esters Against P388 Lymphocytic Leukemia in Mice

| Example | R Group | Vehicle[a] | Dose mg./kg./inj.[b] | Animal weight difference T-C | T/C[c], % |
|---|---|---|---|---|---|
| 1A | $-\overset{O}{\overset{\|\|}{C}}-\overset{O}{\overset{\|\|}{C}}OCH_2CH_3$ | D | 20 | 0.1 | 135 |
| B |  | D | 20 | −0.2 | 211 |
| C |  | D | 13 | −0.8 | 154 |
| D |  | T | 20 | −0.1 | 129 |
| 2A | $-\overset{O}{\overset{\|\|}{C}}-CH=CH-\overset{O}{\overset{\|\|}{C}}-OCH_3$ | B | 80 | −0.7 | 145 |
| B |  | B | 40 | −0.9 | 134 |
| C |  | B | 20 | −1.0 | 125 |
| D |  | B | 10 | −1.2 | 136 |
| E |  | D | 4.4 | −1.5 | 147 |
| F |  | D | 1.9 | 0.5 | 134 |
| 3A | $-\overset{O}{\overset{\|\|}{C}}-\overset{CH_2}{\overset{\|\|}{C}}-CH_2-\overset{O}{\overset{\|\|}{C}}-OCH_3$ | D | 365 | −3.0 | 198[d] |
| B |  | D | 240 | −1.4 | 169 |
| C |  | D | 160 | −0.1 | 183 |
| D |  | D | 160 | −1.1 | 167 |
| E |  | D | 80 | −0.1 | 173 |
| F |  | D | 40 | −1.3 | 135 |
| 4A | $-\overset{O}{\overset{\|\|}{C}}-CH=CH-CH=CH-CH_3$ | D | 80 | 0.9 | 150 |
| B |  | D | 40 | −1.8 | 125 |
| C |  | D | 20 | 0.9 | 130 |
| 5A | $\begin{array}{c}O-\overset{O}{\overset{\|\|}{C}}-OCH_2CCl_3\\ -\overset{O}{\overset{\|\|}{C}}-CH-C_6H_5\end{array}$ | A | 320 | −2.3 | 136 |
| B |  | A | 160 | 1.2 | 154 |
| C |  | A | 80 | −1.0 | 138 |
| 6A | $-\overset{O}{\overset{\|\|}{C}}-OCH_2CCl_3$ | D | 320 | −1.0 | 172 |
| B |  | D | 160 | −0.9 | 162 |
| C |  | D | 160 | −0.3 | 155 |
| D |  | D | 80 | −0.9 | 183 |
| E |  | D | 80 | −1.3 | 160 |
| F |  | D | 40 | −0.4 | 140 |
| G |  | D | 40 | 0.9 | 183 |
| H |  | D | 20 | −2.7 | 128 |
| I |  | D | 20 | −1.5 | 160 |
| J |  | D | 20 | −1.0 | 195 |
| K |  | D | 13 | −0.5 | 138 |
| L |  | D | 8.8 | −0.3 | 170 |

[a]A = saline, B = water + alcohol + acetone, C = water + acetone, D = water + alcohol, T = saline + Tween 80.
[b]One intraperitoneal injection per day for 9 days; DBA/2 mice.
[c]T/C = mean survival time of test animals/mean survival time of control animals; 125% or above considered active. Unaccountable variations in T/C values among duplicate tests were sometimes observed; these may possibly be due to solubility properties of the esters in the vehicles used.
[d]One 30-day cure was reported.

Dose levels other than those indicated in Table II were tested but gave either toxic or inactive responses. The terms "effective amount" and "effective dose" as referring to the treatment of animals is defined herein to mean those quantities of cephalotaxine ester which will cause remission of the leukemia in the animal to which it is administered, without imparting a toxic response. The effective amount will vary with the particular esters, the injection vehicle, the strain of leukemia, and other related factors. Generally for the instant esters, an effective dose will be in the range of about 1.5-380 mg./kg. of body weight/day. The preferred dose range for a given ester is defined by the lowest and highest dose shown in Table II for that ester.

The activities of these novel cephalotaxyl esters are not predictable, and in some cases are totally unexpected from structure-activity correlations based upon the naturally occurring active esters and certain other synthetic esters. For instance, all of the naturally occurring active esters, such as harringtonine, homoharringtonine, and deoxyharringtonine, contain a dicarboxylic acyl group and a tertiary hydroxyl group alpha to the carboxyl esterified with the cephalotaxine molecule. The hydroxyl group is notably absent in all of our compounds, and the trans,trans-sorbate of Example 4 and the trichloroethylcarbonate of Example 6 do not exhibit the dicarboxylic acid moiety. Eighteen other acyl esters, synthesized at approximately the same time as the subject acyl esters, were inactive. For example, the cephalotaxyl ester of mandelic acid, without the trichloroethylcarbonate moiety appearing in the compound of Example 5, had no activity. In addition, toxicity observed during administration of the mandelic acid ester at doses above 80 mg./kg./injection is not present with the trichloroethylcarbonate mandelic acid ester at doses up to 320 mg./kg./injection. On the other hand, the trichloroethylcarbonate of cephalotaxyl α-hydroxy-α-methyl butyrate is inactive. Likewise, the ethyl carbonate, benzyl carbonate, and chloro acetate esters of cephalotaxine are inactive. The same unpredictability occurs with compounds related to the itaconate ester of Example 3 by virtue of having α,β-unsaturation or α,β-unsaturation coupled with a second carboxyl group. Thus, the methyl 2-methyl-2-butendioate, methyl muconate, acrylate, methacrylate, cinnamate, and p-nitrocinnamate esters of cephalotaxine are all inactive.

It is understood that the foregoing detailed description is given merely by way of illustration and that modification and variations may be made therein without departing from the spirit and scope of the invention.

We claim:

1. A method of treating animals for remission of leukemia of the strain P388 comprising administering to said animals by injection an amount, effective for said remission, of an active alkaloid compound having the following structure:

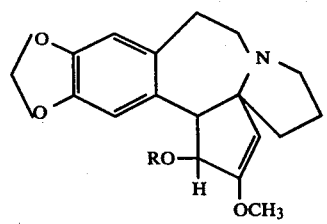

where R is selected from the group consisting of

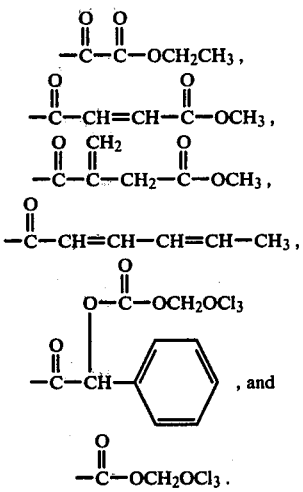

2. The method as described in claim 1 wherein R is

3. The method as described in claim 1 wherein R is

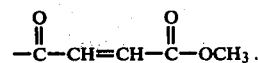

4. The method as described in claim 1 wherein R is

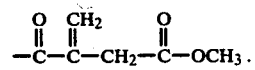

5. The method as described in claim 1 wherein R is

6. The method as described in claim 1 wherein R is

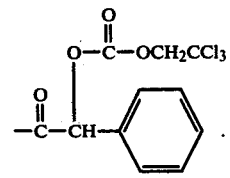

7. The method as described in claim 1 wherein R is

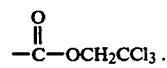

* * * * *